United States Patent
Speiser et al.

(10) Patent No.: US 6,864,209 B2
(45) Date of Patent: Mar. 8, 2005

(54) ORGANOMETALLIC COMPLEXES COMPRISING PHOSPHONITE LIGANDS, AND THEIR USE IN CATALYZING OLEFIN OLIGOMERIZATION

(75) Inventors: Fredy Speiser, Schiltigheim (FR); Pierre Braunstein, Strasbourg (FR); Lucien Saussine, Croissy sur Seine (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 10/402,153

(22) Filed: Mar. 31, 2003

(65) Prior Publication Data

US 2003/0216251 A1 Nov. 20, 2003

(30) Foreign Application Priority Data

Mar. 29, 2002 (FR) .......................................... 02 04107

(51) Int. Cl.[7] ........................... B01J 31/00; B01J 37/00; C08F 4/02; C08F 4/60; C08F 4/44
(52) U.S. Cl. ........................ 502/117; 526/161; 526/169
(58) Field of Search ......................... 502/117; 526/161, 526/169

(56) References Cited

U.S. PATENT DOCUMENTS 4,025,570 A  5/1977  Cramer

OTHER PUBLICATIONS

Patent Abstract of Japan—vol. 1998, No. 02, Jan. 30, 1998, and JP 09 268 132 A (Mitsubishi Chem Corp), Oct. 14, 1997.
XP–002224757—Organometallics 2000, 19, 2676–2683, Ruthenium Complexes with Novel Tridentate N,P,N Ligands Containing a Phosphonite Bridge between Two Chiral Oxazollnes. Catalytic Activity in Cyclopropanation of Olefins and Transfer Hydrogenation of Acetophenone, Pierre Braunstein et al.

Primary Examiner—Mark L. Bell
Assistant Examiner—J. Pasterczyk
(74) Attorney, Agent, or Firm—Millen, White, Zelano & Branigan, P.C.

(57) ABSTRACT

A catalytic composition for oligomerizing olefins, in particular ethylene, comprises mixing at least one nickel complex, prepared by reacting a nickel salt with a phosphonite ligapd, with at least one hydrocarbylaluminum compound in a molar proportion with respect to the nickel of not more than 8" and selected from the group formed by tris(hydrocarbyl)aluminum compounds, chlorinated or brominated hydrocarbylaluminum compounds and aluminoxanes.

25 Claims, No Drawings

ORGANOMETALLIC COMPLEXES COMPRISING PHOSPHONITE LIGANDS, AND THEIR USE IN CATALYZING OLEFIN OLIGOMERIZATION

BACKGROUND OF THE INVENTION

1. Field of the Invention

The present invention relates to olefin oligomerization, in particular ethylene oligomerization.

In a first aspect, the invention provides a novel catalytic composition. In a further aspect, the invention provides a process for oligomerizing olefins, in particular ethylene, using said catalytic composition.

2. Description of the Prior Art

It is well known that α-mono-olefins such as ethylene, propylene or 1-butene can be oligomerized with catalytic systems based on transition metals such as nickel, chromium, titanium, zirconium or other metals, in the presence of a co-catalyst such as a hydrocarbylaluminum compound, a hydrocarbylaluminum compound or an aluminoxane. However, many Ziegler-Natta type catalysts have low activity when the proportion of co-catalyst is small, and result in a large consumption of co-catalyst since a mole ratio of aluminum to transition metal of more than 10 is often necessary to obtain a sufficiently active catalyst.

SUMMARY OF THE INVENTION

It has now been found that, unexpectedly, a catalytic composition obtained by mixing at least one nickel complex containing at least one phosphonite type ligand in combination with at least one hydrocarbylaluminum compound in a relatively low proportion compared to 10:1 of prior art catalysts, has an improved activity for olefin oligomerization, in particular ethylene oligomerization.

DETAILED DESCRIPTION OF THE INVENTION

The catalytic composition of the invention is defined as comprising a mixture:

of at least one nickel complex containing at least one phosphonite ligand having the general formula $LNiX_2$ in which L is a bidentate or tridentate phosphonite ligand with general formula:

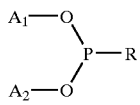

in which R represents a monovalent hydrocarbon radical containing up to 12 carbon atoms and radicals $A_1$—O— and $A_2$—O—, which may be identical or different, are selected from alkoxy radicals carrying a nitrogen-containing heterocycle and X is a halide anion, an acetylacetonate anion or a carboxylate anion;

with at least one hydrocarbylaluminum compound selected from the group formed by tris(hydrocarbyl) aluminum compounds, chlorinated or brominated hydrocarbylaluminum compounds with general formula $AlR''_m Y_{3-m}$ in which R'' is a hydrocarbyl radical containing 1 to 6 carbon atoms, Y is a chlorine or bromine atom and m is a number from 1 to 3, and aluminoxanes;

in an Al/Ni mole ratio of 8/1 or less.

More precisely, in the general formula of the bidentate or tridentate phosphonite ligand:

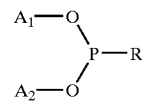

$A_1$—O— and $A_2$—O—, identical or different, can be selected from alkoxy-pyridine and alkoxy-oxazoline radicals. More precisely, radicals $A_1$—O— and $A_2$—O— can have the following general formulae:

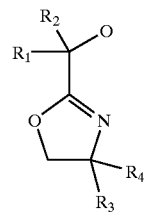

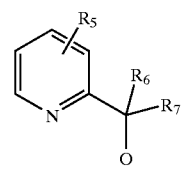

in which radicals $R_1$, $R_2$, $R_3$, $R_4$, $R_5$, $R_6$ and $R_7$, which may be identical or different, are selected from a hydrogen atom, linear or branched alkyl radicals, aryl, aralkyl or alkaryl radicals containing 1 to 12 carbon atoms. Radical $R_5$ can be at any one of the free positions in the aromatic ring. By way of non-limiting example, said substituents can be selected from methyl, ethyl, isopropyl, isobutyl, tert-butyl, cyclohexyl, phenyl and benzyl radicals.

In formula 1, radicals $A_1$ and $A_2$ can be identical, for example in the ligands shown below:

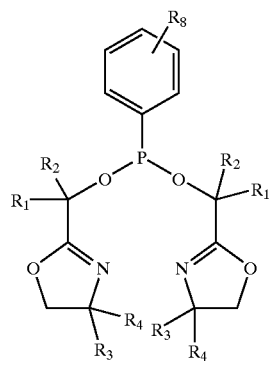

-continued

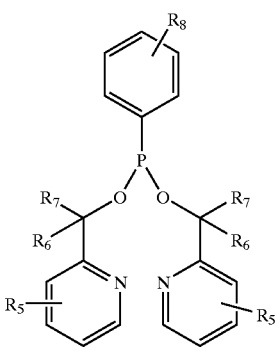

5

Further, in formula 1, radicals R and $A_1$, R and $A_2$ or $A_1$ and $A_2$ can be bonded together and form part of the same cyclic radical, such as those shown in the formulae below:

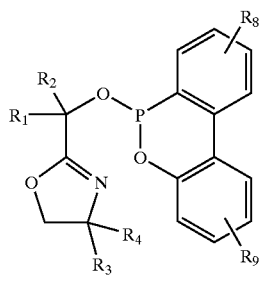

6

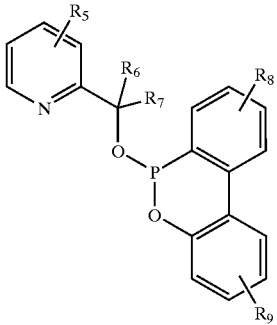

7

In formulae 4 to 7 above, radicals $R_1$, $R_2$, $R_3$, $R_4$, $R_5$, $R_6$, $R_7$, $R_8$ and $R_9$ have the definitions given above for radicals $R_1$, $R_2$, $R_3$, $R_4$, $R_5$, $R_6$ and $R_7$.

In the formula for the nickel complex, X can be a Cl, Br or I halogen anion, an acetylacetonate, acetate or trifluoroacetate anion or more generally a carboxylate anion R'COO⁻ in which R' is a hydrocarbyl radical, for example alkyl, cycloalkyl, alkenyl, aryl, aralkyl or alkaryl containing up to 20 carbon atoms, preferably a hydrocarbyl radical containing 5 to 20 carbon atoms, optionally substituted with halogen atoms (fluorine or chlorine). The carboxylate anion can be selected from the following non-limiting anions: octoate, 2-ethylhexanoate, stearate, oleate, naphthenate and adipate.

The hydrocarbylaluminum compounds are selected from the group formed by tris(hydrocarbyl)aluminum compounds, chlorinated or brominated hydrocarbylaluminum compounds and aluminoxanes. Preferably, the tris (hydrocarbyl)aluminum compounds and the chlorinated or brominated hydrocarbylaluminum compounds have general formula $AlR''_mY_{3-m}$ in which R" represents a monovalent hydrocarbon radical containing up to 12 carbon atoms, for example, such as alkyl, aryl, aralkyl, alkaryl or cycloalkyl, Y represents a halogen atom selected from chlorine and bromine, for example, Y preferably being a chlorine atom, m takes a value of 1 to 3, with m preferably being equal to 1.

Examples of such compounds with formula $AlR''_mY_{3-m}$ that can be mentioned are ethylaluminum sesquichloride, dichloroethylaluminum, dichloroisobutylaluminum, chlorodiethylaluminum and triethylaluminum.

The phosphonite type ligands are prepared using the methods described in the literature (P Braunstein et al., Organometallics 2000, 19, 2676–2683).

The nickel complex $LNiX_2$ is prepared using methods that are known in the literature for synthesizing nickel complexes with a neutral ligand. Any process for preparing this compound is suitable, such as reacting the phosphonite ligand with a nickel salt in an organic solvent, for example an ether, an alcohol or a chlorinated solvent such as dichloromethane. The complex can be prepared in situ in the solvent used for the oligomerization reaction. In this case, the order for mixing the nickel salt and the phosphonite ligand is not critical. However, it is preferable to prepare in the first instance a solution of a nickel salt that is soluble in an organic medium such as a nickel carboxylate and then to add the phosphonite ligand.

The nickel complex and the aluminum co-catalyst can be brought into contact in a solvent constituted by a saturated hydrocarbon such as hexane, cyclohexane, heptane, butane or isobutane, by an unsaturated hydrocarbon such as a mono-olefin or a di-olefin containing 4 to 20 carbon atoms, for example, or by an aromatic hydrocarbon such as benzene, toluene, ortho-xylene, mesitylene, ethylbenzene or chlorobenzene, used pure or as a mixture.

The nickel concentration in the catalytic solution is generally from $1\times10^{-5}$ to 0.1 moles/l, preferably $5\times10^{-5}$ to $1\times10^{-2}$ moles/l.

The mole ratio between the hydrocarbylaluminum and the nickel complex is in the range 1/1 and 8/1, preferably in the range 1/1 to 6/1.

The order in which the two constituents of the catalytic composition is mixed is not critical. However, it is preferable to add the hydrocarbylaluminum compound to the solution of the complex.

The ethylene oligomerization reaction can be carried out at a total pressure of 0.5 to 15 MPa, preferably 1 to 8 MPa, and at a temperature of 20° C. to 180° C., preferably 40° C. to 140° C.

In a particular batchwise implementation of the catalytic oligomerization reaction, a selected volume of the catalytic solution constituted as described above is introduced into a reactor provided with the usual stirring, heating and cooling means, then it is pressurized to the desired pressure with ethylene, and the temperature is adjusted to the desired value. The oligomerization reaction is kept at constant pressure by introducing ethylene until the total volume of liquid produced represents 2 to 50 times the volume of the catalytic solution originally introduced, for example. The catalyst is then destroyed by any usual means known to the skilled person then the reaction products and solvent are extracted and separated out.

With a continuous operation, the following implementation is employed, for example: the catalytic solution is injected at the same time as ethylene into a reactor stirred by conventional mechanical means or by external re-circulation, and kept at the desired temperature. It is also possible to separately inject the components of the catalyst into the reaction medium, for example the nickel complex comprising the phosphonite ligand and the hydrocarbylaluminum compound. The ethylene is introduced via a pressure controlled inlet valve which keeps the pressure constant. The reaction mixture is withdrawn by means of a liquid level controlled valve which keeps the liquid level constant. The catalyst is continuously destroyed by any conventional means known to the skilled person, then the reaction products and the solvent are separated, for example by distillation. Untransformed ethylene can be recycled to the reactor.

The following examples illustrate the invention without limiting its scope.

EXAMPLE 1 a) Preparation of (NOPON)NiCl$_2$ Complex

The phosphonite ligand 4 for which $R_1=R_2=R_3=R_4=$ methyl and $R_8=$H, abbreviated to NOPON, was prepared using the methods described in the literature (P Braunstein et al., Organometallics 2000, 19, 2676–2683).

The phosphonite ligand 4 (0.420 g, 0.998 mole) was dissolved in 30 ml of tetrahydrofuran (THF) then, after adding one equivalent of nickel chloride-dimethylether, NiCl$_2$(DME) (0.217 g, 0.998 mmole), the solution was stirred for 24 hours. After evaporating off the solvent, the green complex was taken up in dichloromethane, the solution was filtered over celite, then concentrated. The green solid was vacuum dried. Yield: 0.660 g, i.e., 75%. This product was characterized by an infrared absorption band at 1620 cm$^{-1}$, characteristic of the C=N double bond coordinated to nickel.

b) Ethylene Oligomerization 0.1×10$^{-3}$ moles of nickel complex diluted with 25 ml of distilled toluene and stored in an inert atmosphere was introduced, protected from air and moisture, into a 50 ml glass flask placed in an inert atmosphere. 10 ml of the nickel solution prepared above, i.e., 0.04×10$^{-3}$ moles of nickel, and 0.08×10$^{-3}$ moles of dichloroethylaluminum in solution in 5 ml of toluene were introduced in that order into a stainless steel autoclave with a useful volume of 100 ml provided with a jacket for regulating the temperature by oil circulation. The temperature was raised to 30° C. and the ethylene pressure was kept at 1 MPa.

After 70 minutes of reaction, ethylene introduction was stopped and the reactor was cooled and degassed, then the gas and the liquid which had been withdrawn with a syringe were analyzed by gas chromatography. 35 g of ethylene had been consumed in 70 minutes. The composition of the products is shown in Table 1. The growth factor for the geometrical Schulz-Flory (SF) distribution is represented by $k_\alpha$.

EXAMPLE 2

Using the same apparatus as that described for Example 1 and the same conditions with the exception that the ratio of the dichloroethylaluminum to the nickel was 6/1 instead of 2/1, 41 g of ethylene was consumed in 70 minutes of reaction. The composition of the products is shown in Table 1.

EXAMPLE 3 a) Preparation of Nickel Complex

The procedure of Example 1 was used to prepare the complex, with the exception that the ligand used to complex the nickel had formula 7 with $R_5=$H, $R_6=R_7=$methyl, $R_8=R_9=$H.

Synthesis of ligand 7: the starting products were prepared using published methods: S D Pastor et al., "Phosphorus and Sulphur", 1987, vol 31, p 71, for 6-chloro-6H-dibenz[c,c][1,2] oxaphosphorine, and D S Noyce et al., J Org Chem 1973, 38, 2260, for 2-(2-pyridyl)-2-propanol.

A solution of 2-(2-pyridyl)-2-propanol (0.580 g, 4.26 mmole) in 30 ml of tetrahydrofuran was cooled to −78° C. then stirred for one hour after adding one equivalent of butyllithium. A solution of 6-chloro-6H-dibenz[c,e] [1,2] oxaphosphorine (1 g, 4.26 mmole) in solution in 20 ml of tetrahydrofuran was then added dropwise and the mixture was allowed to warm up slowly to 20° C. with stirring over about 15 hours. After hydrolysis with degassed water, extraction with ether, drying the organic phase over MgSO$_4$ and evaporating off the solvent, 1.16 g of a yellow oil was obtained in a yield of 80%.

$^1$H-NMR (CDCl$_3$):

δ (ppm): 1.74 (3H, C(CH$_3$)$_2$), 1.76 (3H, C(CH$_3$)$_2$), 7.17–7.35 (m, 4H, OPh), 7.65 (m, 1H, py-H$_4$), 7.44 (m, 1H, py-H$_5$), 7.60 (m, 1H, py-H$_3$), 7.43–8.04 (m, 4H, P Ph), 8.04 (t, 1H, py-H$_4$, $^3$J(H,H)=6.0 Hz), 9.2 (d, 1H, py-H$_6$, $^3$J(H,H)=8.1 Hz)

$^{31}$P-NMR (CDCl$_3$):

δ (ppm): 119.8 b) Ethylene Oligomerization

The apparatus described and used in Example 1 was employed under the same conditions. The ratio of dichloroethylaluminum to nickel was 2/1. The composition of the products is shown in Table 1.

EXAMPLE 4

The procedure of Example 3 was followed with the exception that the ratio of dichloroethylaluminum to nickel was 6/1 instead of 2/1.

EXAMPLE 5 a) Preparation of Nickel Complex

The procedure of Example 1 was employed, with the exception that the ligand used to complex the nickel had formula 6 with $R_1=R_2=R_3=R_4=$methyl, $R_8=R_9=$H.

Ligand 6 was prepared in a yield of 75% using methods described in the literature by reacting 4,4'-dimethyl-2-(1-hydroxy-1-methylethyl)-4,5-dihydrooxazole with 6-chloro-6H-dibenz[c,e] [1,2] oxaphosphorine, in the presence of triethylamine (see references above).

$^1$H-NMR (CD$_2$Cl$_2$):

δ (ppm): 1.30 (6H), 1.38 (3H); 1.62 (3H); 4.01 (2H), 7.1–7.7 (m, 6H), 7.98 (m, 2H).

$^{31}$P-NMR (CD$_2$Cl$_2$):

δ (ppm): 120.9 b) Ethylene Oligomerization

The apparatus described and used in Example 1 was employed under the same conditions. The ratio of dichloroethylaluminum to nickel was 2/1. The composition of the products is shown in Table 1.

TABLE 1

| Example | Distribution of oligomers (wt %) | | | | $k_\alpha$ SF | Productivity (g ethylene/g of Ni/h) |
| --- | --- | --- | --- | --- | --- | --- |
| | C4 | C6 | C8 | C10+ | | |
| 1 | 75.8 | 22.2 | 1.8 | 0.2 | 0.14 | 12,700 |
| 2 | 70.4 | 26.8 | 2.6 | 0.2 | 0.16 | 15,000 |
| 3 | 81.4 | 17.0 | 1.4 | 0.2 | 0.11 | 21,100 |
| 4 | 74.8 | 22.5 | 2.5 | 0.2 | 0.15 | 27,400 |
| 5 | 72.9 | 25.5 | 1.5 | 0.1 | 0.17 | 21,200 |

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications cited above and below, and of corresponding French application 02/04,107, filed Mar. 29, 2002, are hereby incorporated by reference.

From the foregoing-description, one skilled in the art can easily ascertain the essential characteristics of this invention and, without departing from the spirit and scope thereof, can make various changes and modifications of the invention to adapt it to various usages and conditions.

What is claimed is:

1. A catalytic composition comprising a mixture of:
   at least one nickel complex containing at least one phosphonite ligand having the general formula $LN_1X_2$ in which L is a bidentare or trideniate phosphonite ligand with general formula:

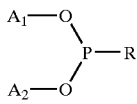

in which R represents a monovalent hydrocarbon radical containing up to 12 carbon atoms, and radicals $A_1$—O— and $A_2$—O—, which are identical or different, are alkoxy radicals carrying a nitrogen-containing heterocycle, and X is a halide anion, an acerylacetonate anion or a carboxylate anion;
   with at least one hydrocarbylaluminum compound selected from the group consisting of tris(hydrocarbyl) aluminum compounds, chlorinated and brominated hydrocarbylaluminum compounds with general formula $AlR''_mY_{3-m}$ in which R" is a hydcocarbyl radical containing 1 to 6 carbon atoms, Y is a chlorine or bromine atom and m is a number from 1 in 3, and aluminoxanes;
   in an Al/Ni mole ratio of 8/1 or less.

2. A composition according to claim 1, wherein R represents an alkyl, aryl, aralkyl, alkaryl, cycloalkyl or substituted aryl radical.

3. A composition according to claim 1, wherein in the phosphonite ligand, radicals $A_1$—O— and $A_2$—O—, which are identical or different, are optionally substituted alkoxy-pyridine or alkoxy-oxazoline radicals.

4. A composition according to claim 3, wherein that each of radicals $A_1$—O— and $A_2$—O— has one of the following general formulae:

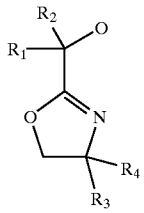 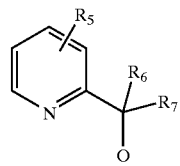

in which radicals $R_1$, $R_2$, $R_3$, $R_4$, $R_5$, $R_6$ and $R_7$, which are identical or different, are each a hydrogen atom, linear or branched alkyl radical, or aryl, aralkyl or alkaryl radical containing 1 to 12 carbon atoms, and radical $R_5$ is at any one of the free positions in the aromatic ring.

5. A composition according to claim 1, wherein in the nickel complex, X represents a Cl, Br or I anion, acetylacetonate, acetate or trifluoroacetate.

6. A composition according to claim 1, wherein the phosphonite ligand has one of the following general formulae:

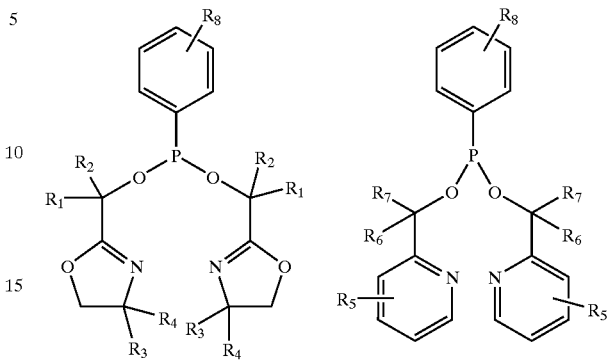

in which radicals $R_1$, $R_2$, $R_3$, $R_4$, $R_5$, $R_6$, $R_7$ and $R_8$ are identical or different and are each a hydrogen atom, linear or branched alkyl radical and aryl, aralkyl or alkaryl radicals containing 1 to 12 carbon atoms, and $R_5$ and $R_8$ are each at any one of the free positions in the aromatic ring.

7. A composition according to claim 1, wherein the phosphonite ligand has one of the following general formulae:

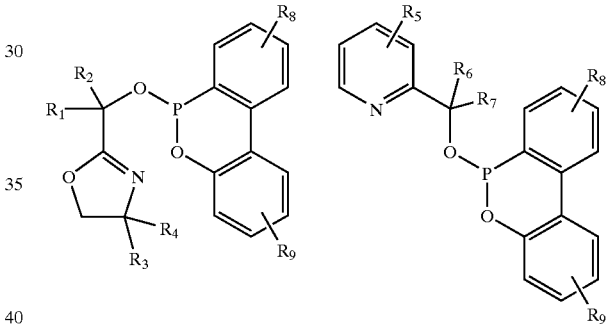

in which radicals $R_1$, $R_2$, $R_3$, $R_4$, $R_5$, $R_6$, $R_7$ and $R_8$ are $R_9$ identical or different and are each a hydrogen atom, linear or branched alkyl radical and aryl, aralkyl or alkaryl radical containing 1 to 12 carbon atoms, and $R_5$, $R_8$ and $R_9$ are each at any one of the free positions in the aromatic ring.

8. A composition according to claim 1, wherein the hydrocarbylaluminum compound is dichloroethylaluminum, ethylaluminum sesquichloride, chlorodiethylaluminum, chlorodiisobutylaluminum, triethylaluminum, tripropylaluminum, triisobutylaluminum or methylaluminoxane.

9. A composition according to claim 8, wherein said hydrocarbylaluminum compound is chlorodiethylaluminum.

10. A composition according to claim 1, wherein the components of the catalyst are brought into contact in a solvent comprising a saturated, olefinic unsaturated or aromatic hydrocarbon to form a catalytic solution.

11. A composition according to claim 10, wherein the concentration of nickel in the catalytic solution is in the range $1\times10^{-5}$ to 0.1 moles/l.

12. A composition according to claim 1, wherein the mole ratio between the hydrocarbylaluminum and the nickel complex is in the range of 1/1 and 8/1.

13. In a process comprising catalytically oligomerizing ethylene, the improvement wherein the catalyst is according to claim 1.

14. A process according to claim 13, wherein the ethylene oligomerization reaction is carried out at a pressure of 0.5 to 15 MPa and at a temperature of 20° C. to 180° C.

15. A composition according to claim 11, wherein the mole ratio between the hydrocarbylaluminum and the nickel complex is in the range of 1/1 and 8/1.

16. A composition according to claim 4, wherein the hydrocarbylaluminum compound is dichloroethylaluminum, ethylaluminum sesquichloride, chlorodiethylaluminum, chlorodiisobutylaluminum, triethylaluminum, tripropylaluminum, triisobutylaluminum or methylaluminoxane.

17. A composition according to claim 1, wherein the Al/Ni mol ratio is in the range of 6/1 to 1/1.

18. A composition according to claim 4, wherein the Al/Ni mol ratio is in the range of 6/1 to 1/1.

19. A composition according to claim 6, wherein the Al/Ni mol ratio is in the range of 6/1 to 1/1.

20. A composition according to claim 7, wherein the Al/Ni mol ratio is in the range of 6/1 to 1/1.

21. A composition according to claim 4, wherein $R_1$, $R_2$, $R_3$, $R_4$, $R_5$, $R_6$ and $R_7$, which are identical or different, are each methyl, ethyl, isopropyl, isobutyl, tert-butyl, cyclohexyl, phenyl or benzyl.

22. A composition according to claim 1, wherein X is a carboxylate anion of the formula R'COO in which R' is alkyl, cycloalkyl, alkenyl, aryl, aralkyl or alkaryl, in each case having up to 20 carbon atoms and in each case optionally substituted with fluorine or chlorine.

23. A composition according to claim 10, wherein said solvent is hexane, cyclohexane, heptane, butane, isobutene, a mono-olefin containing 4 to 20 carbon atoms, a di-olefin containing 4 to 20 carbon atoms, benzene, toluene, ortho-xylene, mesitylene, ethylbenzene, or chlorobenzene.

24. A composition according to claim 16, wherein the phosphonite ligand has one of the following general formulae:

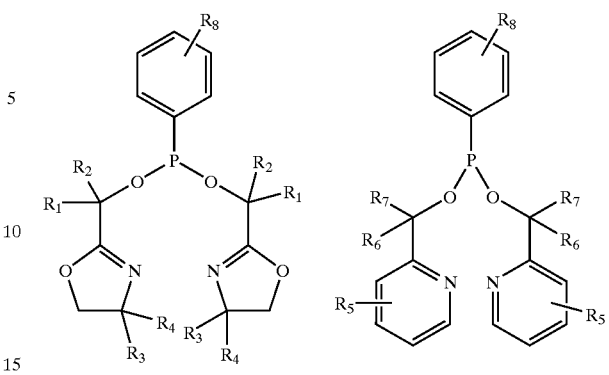

in which radicals $R_1$, $R_2$, $R_3$, $R_4$, $R_5$, $R_6$, $R_7$ and $R_8$ are identical or different and are each a hydrogen atom, linear or branched alkyl radical, or aralkyl or alkaryl radical containing 1 to 12 carbon atoms, and $R_5$ and $R_8$ are each at any one of the free positions in the aromatic ring.

25. A composition according to claim 16, wherein the phosphonite ligand has one of the following general formulae:

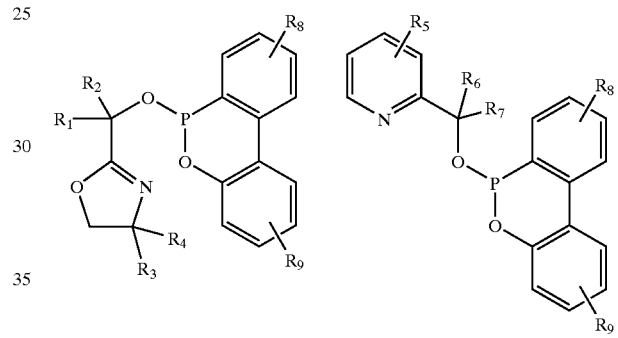

in which radicals and $R_1$, $R_2$, $R_3$, $R_4$, $R_5$, $R_6$, $R_7$, $R_8$ and $R_9$ are identical or different and are each a hydrogen atom, linear or branched alkyl radical, or aryl, aralkyl or alkaryl radical containing 1 to 12 carbon atoms, and radicals $R_5$, $R_8$, and $R_9$ are each at any one of the free positions in the aromatic ring.

* * * * *

UNITED STATES PATENT AND TRADEMARK OFFICE
CERTIFICATE OF CORRECTION

PATENT NO. : 6,864,209 B2  Page 1 of 1
DATED : March 8, 2005
INVENTOR(S) : Fredy Speiser et al.

It is certified that error appears in the above-identified patent and that said Letters Patent is hereby corrected as shown below:

<u>Column 7,</u>
Line 16, reads "bidentare" should read -- bidentate --.
Line 16, reads "trideniate" should read -- tridentate --.
Line 36, reads "1 in 3" should read -- 1 to 3 --.

<u>Column 8,</u>
Line 42, reads "$R_7$ and $R_8$ are $R_9$" should read -- R7,R8 and R9 are --.

<u>Column 10,</u>
Line 19, add -- aryl, -- after first occurrence of "or".
Line 39, delete first occurrence of "and".

Signed and Sealed this

Twenty-eighth Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,864,209 B2
DATED : March 8, 2005
INVENTOR(S) : Fredy Speiser et al.

It is certified that error appears in the above-identified patent and that said Letters Patent is hereby corrected as shown below:

Column 7,
Line 15, reads "$LN_1X_2$" should read -- $LNiX2$. --.

Signed and Sealed this

Thirtieth Day of May, 2006

JON W. DUDAS
*Director of the United States Patent and Trademark Office*